(12) United States Patent
Nashed

(10) Patent No.: US 8,826,909 B2
(45) Date of Patent: *Sep. 9, 2014

(54) RESPIRATORY FACE MASK AND HEADSTRAP ASSEMBLY

(76) Inventor: Ramses Nashed, Tierra Verde, FL (US)

( * ) Notice: Subject to any disclaimer, the term of this patent is extended or adjusted under 35 U.S.C. 154(b) by 1262 days.

This patent is subject to a terminal disclaimer.

(21) Appl. No.: 12/221,379

(22) Filed: Aug. 1, 2008

(65) Prior Publication Data

US 2008/0295845 A1    Dec. 4, 2008

Related U.S. Application Data

(63) Continuation-in-part of application No. 11/809,435, filed on Jun. 1, 2007, now Pat. No. 8,336,549.

(51) Int. Cl.
*A61M 16/06*    (2006.01)
*A61M 16/08*    (2006.01)

(52) U.S. Cl.
CPC .............. *A61M 16/06* (2013.01); *A61M 16/085* (2014.02); *A61M 16/0683* (2013.01); *A61M 2230/432* (2013.01); *A61M 16/0833* (2014.02)
USPC ............ 128/206.28; 128/200.24; 128/203.29; 128/203.12; 128/205.25; 128/206.21

(58) Field of Classification Search
CPC ... A41D 13/00; A41D 13/11; A41D 13/1107; A41D 13/1138; A41D 13/1146; A41D 13/1161; A61F 9/02; A61F 9/026; A61F 9/027; A62B 18/00; A62B 18/02; A62B 18/025; A62B 18/08; A62B 18/084; A62B 9/00; A61M 16/00; A61M 16/06; A61M 16/0683; A61M 2016/00; A61M 2016/06; A61M 2016/0605; A61M 2016/0611; A61M 2016/0616; A61M 2016/0622; A61M 2016/0683; A61M 2016/0694

USPC .......... 128/857, 863, 200.24, 201.22, 201.23, 128/201.25, 201.28, 202.27, 203.12, 128/203.13, 203.14, 203.29, 204.18, 128/204.21, 205.25, 206.12, 206.21, 128/206.24, 206.27, 206.28, 206.29, 128/207.11, 207.12, 910–914

See application file for complete search history.

(56) References Cited

U.S. PATENT DOCUMENTS 2,371,965 A * 3/1945 Lehmberg ................ 128/205.25
2,625,155 A * 1/1953 Engelder .................. 128/206.24

(Continued)

FOREIGN PATENT DOCUMENTS

| WO | 01-43804 | 6/2001 |
| WO | 01-70092 | 9/2001 |
| WO | 2005-053542 | 6/2005 |

OTHER PUBLICATIONS

Salter Labs, Salter-Style ETCO2 Divided Sampling Cannula with Simultaneous Oxygen Delivery and Tender Grips. Jul. 2004. Product advertisement.

(Continued)

*Primary Examiner* — Annette Dixon
(74) *Attorney, Agent, or Firm* — Ronald E. Smith; Smith & Hopen, P.A.

(57) ABSTRACT

A respiratory face mask is provided suitably sized and configured to engage the nose portion, mouth portion and chin portion of a patient's face. The face mask is characterized by a cup-like shell or receptacle member defining a peripheral flange and a flexible inflatable hollow sealing cushion on the shell member flange. Headstrap fastener projections extending upright on the flange are adapted to accommodate an elastic headstrap that adjustably may be removably slidingly coupled to the projections to hold the mask in place on a patient's face and head.

5 Claims, 5 Drawing Sheets

(56) References Cited

U.S. PATENT DOCUMENTS

| | | | |
|---|---|---|---|
| 2,875,757 A * | 3/1959 | Galleher, Jr. | 128/206.26 |
| 3,556,097 A * | 1/1971 | Wallace | 128/202.23 |
| 5,265,595 A | 11/1993 | Rudolph | |
| 5,465,712 A * | 11/1995 | Malis et al. | 128/205.25 |
| 5,975,079 A * | 11/1999 | Hellings et al. | 128/206.24 |
| 6,192,886 B1 * | 2/2001 | Rudolph | 128/207.13 |
| 6,263,874 B1 | 7/2001 | LeDez et al. | |
| 6,386,198 B1 * | 5/2002 | Rugless | 128/206.21 |
| 6,860,268 B2 | 3/2005 | Bohn et al. | |
| 6,981,503 B1 * | 1/2006 | Shapiro | 128/845 |
| 7,004,168 B2 | 2/2006 | Mace et al. | |
| 7,243,649 B2 | 7/2007 | Moenning et al. | |
| 7,861,715 B2 * | 1/2011 | Jones et al. | 128/204.21 |
| 8,336,549 B2 * | 12/2012 | Nashed | 128/206.28 |
| 2003/0024533 A1 * | 2/2003 | Sniadach | 128/205.25 |
| 2004/0084048 A1 | 5/2004 | Stenzler et al. | |
| 2006/0000476 A1 * | 1/2006 | Salem | 128/206.21 |

OTHER PUBLICATIONS

Capnoxygen, Not just another oxygen mask. Product advertisement.

Bhananker, S. M.; Posner, K. L.; Cheney, F. W.; Caplan, R. A.; Lee, L. A.; Domino, K. B. Injury and Liability Associated with Monitored Anesthesia Care. Anesthesiology. Feb. 2006, vol. 104, No. 2, pp. 228-234.

SA Rego, M. M.; Watcha, M. F.; White, P. F. The Changing Role of Monitored Anesthesia Care in the Ambulatory Setting. Anesth Analg. 1997. vol. 85, pp. 1020-1036.

* cited by examiner

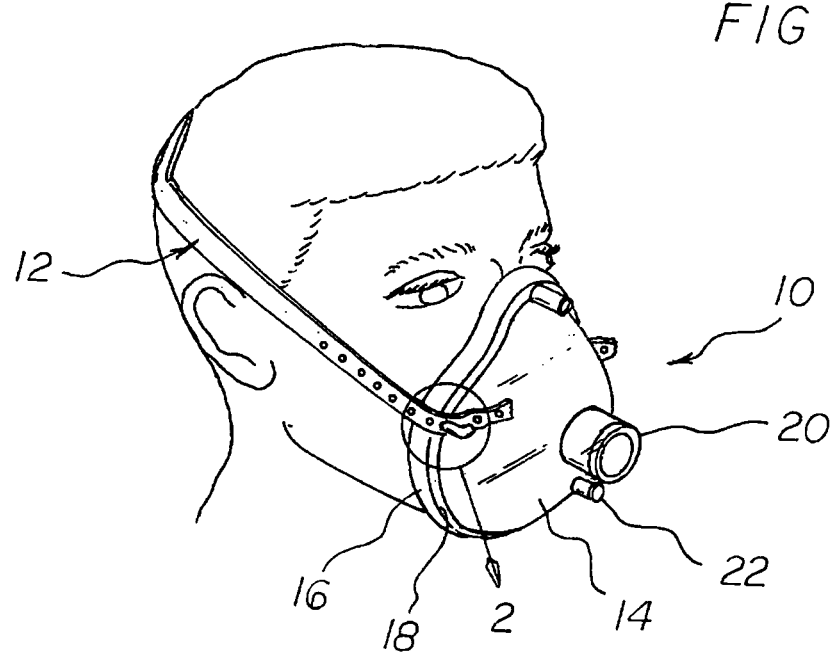
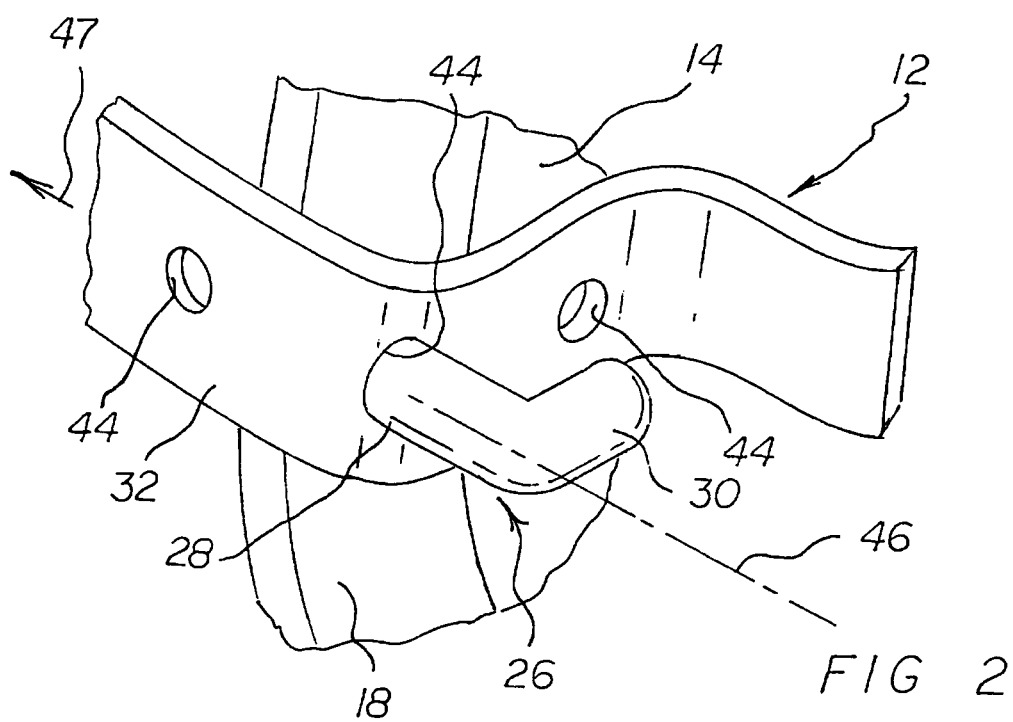

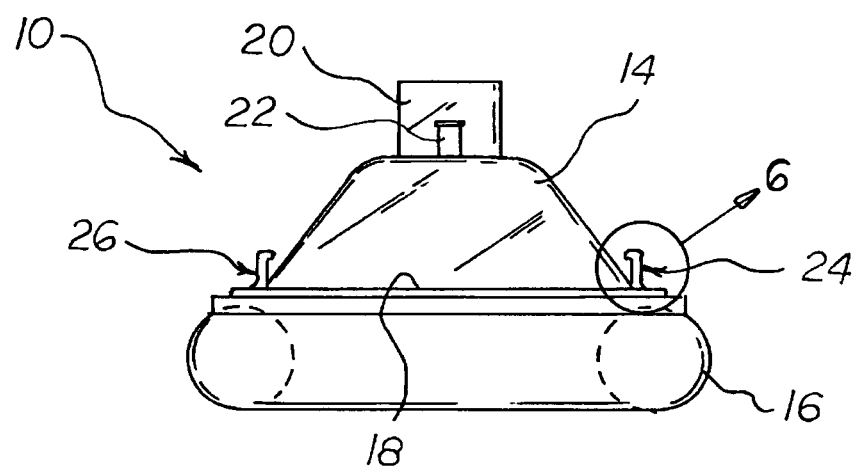
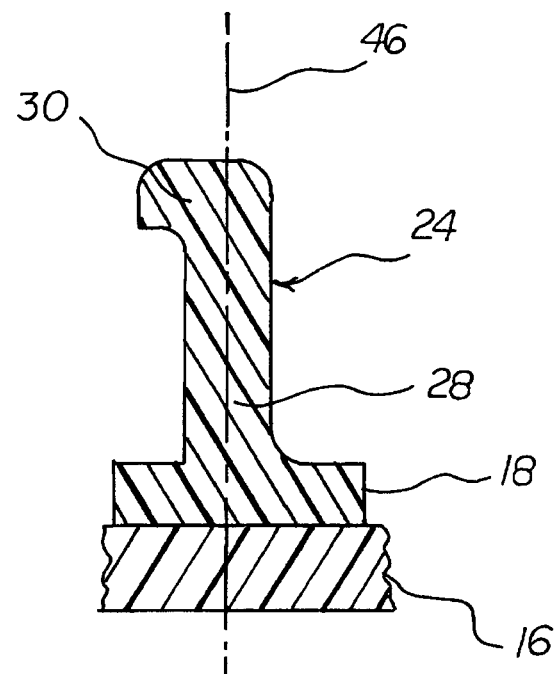

RESPIRATORY FACE MASK AND HEADSTRAP ASSEMBLY

RELATED APPLICATION

The present application is a continuation-in-part (CIP) of my prior U.S. patent application Ser. No. 11/809,435; filed Jun. 1, 2007 now U.S. Pat. No. 8,336,549 (herein "prior application"). The aforesaid prior application hereby is incorporated herein and made part hereof by this reference.

BACKGROUND OF THE INVENTION

1. Field of the Invention

The present application relates generally to devices for delivering respiratory gas or gases in medical applications, and more particularly, to new and improved disposable respiratory face masks which are adapted for use on patients prior to, during or after surgery. Even more particularly, the present invention relates to a respiratory face mask and headstrap assembly that is especially useful in administering gases, such as anesthesia or oxygen, or mixtures of same, for medical purposes, and as such represents an improvement over the similar device or devices disclosed in my prior application.

2. Description of the Prior Art

In my prior application, there is fully disclosed a disposable anesthesia face mask assembly having a flexible hollow inflatable sealing cushion extending along substantially the entire peripheral edge of the mask shell or body member to prevent anesthesia gas or the like delivered through the gas portal on the mask from escaping and adversely affecting the surgical environment. As further disclosed in my prior application, by fitting such a sealable mask on the patient's face and anchoring the bottom portion thereof underneath the chin of the patient, the mask is rendered stable whereas displacement toward the ocular area or elsewhere is prevented under virtually all conditions likely to be encountered during the ensuing surgical procedure, and especially so during relatively long-duration procedures. As disclosed in my prior application, advantageous use of the face mask is facilitated by the employment of a relatively simple headband or strap (preferably elastic) adapted to engage at the strap's opposed free ends only the peripheral rim or edge of the mask body member via strap anchoring lugs projecting laterally and oppositely from the mask rim's edge. By this relatively simple arrangement, the mask may be held comfortably stable on the patient's face without employing excessive strap pressure. Thus, when the mask of my prior application is so used, anesthesia personnel do not have to be concerned about holding the mask in place on the patient's face thereby freeing both hands to attend to other important tasks.

Masks for delivering anesthesia gas, oxygen or the like to patients undergoing surgery are widely used in the administration of general anesthesia (GA), an anesthetic procedure where patients are unable to breathe on their own and this function must be assisted by a ventilator usually through an endo-tracheal tube (intubation) or a laryngeal mask airway (LMA). These prior art masks (used in GA) cover merely the nose and the mouth portions of the patient's face and usually are held in place by the hand or hands of attending anesthesia personnel. Attempts have been made to affix such prior masks to the patient's head and face, but in so doing relatively bulky and cumbersome strap assemblies must be used. These prior strap assemblies, in turn, require relatively excessive pressure to maintain mask stability because of the limited footprint of the mask's pneumatic sealing cushion. For example, U.S. Pat. No. 5,975,079 (Hellings et al) discloses an anesthesia face mask with a removable headstrap plate adapted to fit over the breathing circuit connecting portal extending centrally from the face mask. The plate has four hooks for attachment to a strap assembly which, in turn, features a central body and four attaching prongs connectable respectively to the hooks on the plate.

U.S. Pat. No. 6,981,503 (Shapiro) shows a mask similar to that disclosed in the '079 patent, but furthermore adds a pair of retaining straps 70 and 80 adapted to be placed underneath the patient's chin for attachment to the lower pair of headstrap extensions 64 and 66 (see FIGS. 6 and 7).

The unique face mask assembly disclosed in my prior application represents a significant advance over the foregoing body of prior art because, inter alia, it is the only respiratory or anesthesia mask now known having a pneumatic sealing cushion that extends over and under the chin portion of the patient's face and surprisingly, as a result of this unique arrangement, requires only a relatively simple single headstrap or band for maintaining the mask in a stable position even during long duration surgical procedures. Hence, the mask and headstrap assembly of my prior application is ideally suited for use during so-called "sedation" anesthesia procedures where the patient breathes on its own and which is characterized in the medical art as "Monitored Anesthesia Care" (MAC). The American Society of Anesthesiologists (ASA) defines MAC in part as "a specific anesthesia service in which an anesthesiologist has been requested to participate" and which includes "administration of sedatives, analgesics, hypnotics, anesthetic agents or other medications necessary to ensure patient safety and comfort." As pointed out in my prior application, the face mask assembly disclosed therein may be used to administer anesthesia gas or gases, oxygen, and/or mixtures of same during MAC.

More specifically, with the mask assembly of my prior application, the headstrap opposed ends are adapted to be connected respectively to a pair of lugs projecting laterally from the rim of the mask shell or body. Such lugs may deflect in use causing one or both strap ends to detach and because the lugs are oriented substantially perpendicular to the tension forces in the headstrap, such deflection is more easily effected than desired. Additionally, the attachment headstrap lugs have a T-bar distal end which is relatively difficult to mold and presents the possibility of snagging foreign objects in the surgical environment.

In order to overcome the foregoing disadvantages, the present application discloses a new and improved headstrap and strap attachment system for the mask assembly disclosed in my prior application, or for similar devices.

BRIEF SUMMARY OF THE INVENTION

The present invention, briefly described, essentially comprises the anesthesia face mask of my prior application improved by the addition of a uniquely different headstrap attachment system and headstrap configuration. Rather than the simple strap disclosed in my prior application, the new headstrap disclosed herein comprises an annular shaped pressure-distributing central portion and a pair of arm extension portions extending laterally and oppositely from the central portion. Each arm extension portion includes a series of longitudinally spaced mask-engagement openings or perforations for providing a range of adjustment for different sized patients. Projecting upwardly on the peripheral edge or rim of the mask's body shell or member is a pair of substantially diametrically opposed riser posts for engaging corresponding ends of the strap arm extension portions through a corresponding one of the mask engagement openings in each arm extension portion end portion, respectively. When so engaged, the tension in the headstrap, and in each headstrap arm extension end portion particularly, is directed oppositely to the direction of extent of the corresponding riser post to which it is removably connected, thus providing a surprisingly simple, yet secure strap-to-mask attachment arrangement.

There has thus been described, rather broadly, several important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved respiratory face mask and headstrap assembly which has all of the advantages of the prior art face masks and none of the disadvantages.

It is another object of the present invention to provide a new and improved face mask that especially suitable for use in applying anesthesia inhalation gas or gases to a patient continuously during a relatively long duration surgical procedure.

It is further object of the present invention to provide a new and improved respiratory face mask and headstrap assembly which is of durable and reliable constructions.

An even further object of the present invention is to provide a new and improved respiratory face mask and headstrap assembly which is susceptible of a low cost of manufacture with regard to both materials and labor, and which accordingly is then susceptible of low prices of sale, thereby making such a face mask economically available to the medical community.

Even still another object of the present invention is to provide a new and improved respiratory face mask and headstrap assembly that may be used on a patient before, during or after surgery in a safe and efficient manner.

It is yet another object of the present invention to provide a new and improved respiratory face mask and headstrap assembly where the headstrap comprises an annular shaped pressure-distributing central portion, a pair of arm portions extending laterally and oppositely from the central portion, and wherein each arm portion includes a series of longitudinally spaced mask-engagement openings or perforations for providing a range of adjustment for different sized patients.

Still yet another object of the present invention is to provide a new and improved respiratory face mask and headstrap assembly wherein the headstrap is adapted to be removable attached to the mask in a unique secure manner.

Another object of the present invention is to provide a new and improved respiratory face mask characterized by two primary components, namely a cup-like shell or receptacle member terminating at its peripheral edge in a peripheral flange, and an annular substantially donut-shaped hollow inflatable cushion or sealing member affixed or otherwise permanently attached to the flange along substantially the flange's entire peripheral extent and which further includes upright projections on the flange for accommodating a headstrap that may be suitably removably coupled to the upright projections to hold the mask in place on a patient's face and head.

Yet still another object of the present invention is to provide a respiratory face mask where the mask is characterized by two primary components, namely a cup-like shell or receptacle member terminating at its peripheral edge in a peripheral flange, and an annular substantially donut-shaped hollow inflatable cushion or sealing member affixed or otherwise permanently attached to the flange and which further includes one or more riser posts on the flange for accommodating a headstrap that includes tensionable arm portions and openings in the arm portions such that the direction of extent of the riser posts is opposite to that of the tension force in the headstrap arm portions when they are suitably coupled to the riser posts to hold the mask in place on a patient's face and head by fitting each arm portion to its corresponding riser post through a corresponding opening in each arm portion, respectively.

Even still yet another object of the present invention is to provide a disposable anesthesia face mask and head strap assembly ideally suited for use during so-called "sedation" anesthesia procedures, and especially those characterized in the medical art as "Monitored Anesthesia Care" (MAC).

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the respiratory face mask and headstrap assembly fitted about the head and face of a person.

FIG. 2 is an enlarged fragmentary view in perspective of the portion of the face mask and headstrap assembly indicated by circle 2 in FIG. 1.

FIG. 5 is a view in elevation of the bottom or chin-engaging end of the mask of FIG. 3 as indicated by lines 5-5.

FIG. 7 is an enlarged fragmentary view in perspective of a headstrap riser post mounted on the face mask according to the present invention.

DESCRIPTION OF THE PREFERRED EMBODIMENT

Figure 3:
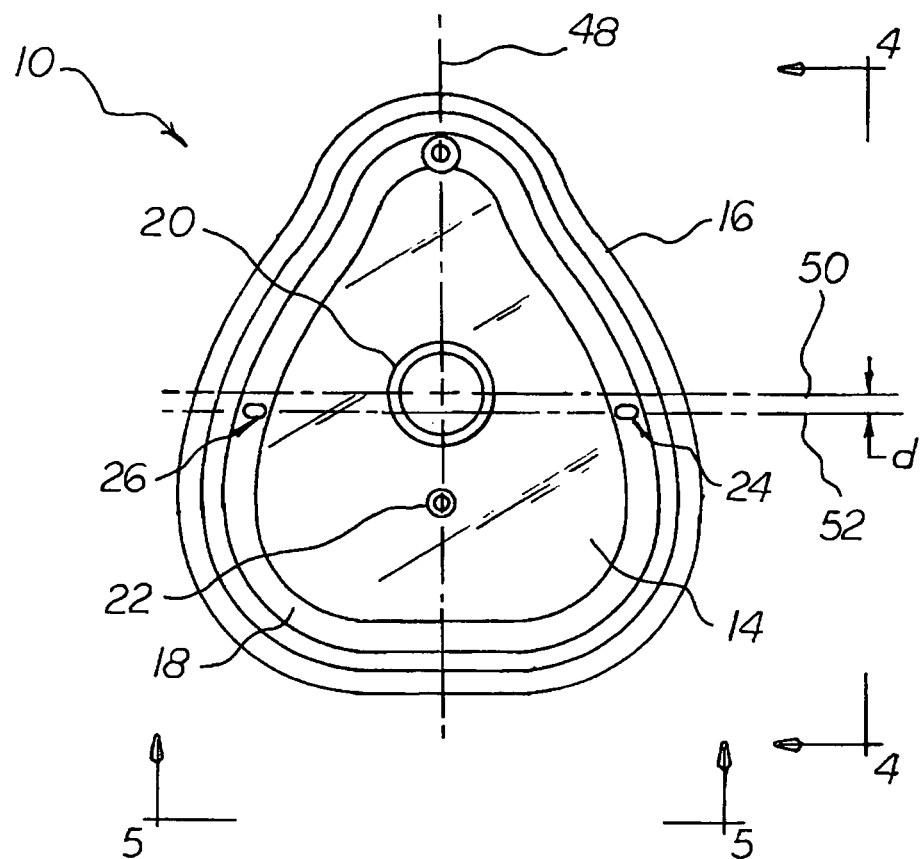
FIG. 3 is a top plan view of the face mask component of FIG. 1 (i.e. without the headstrap).
Figure 4:
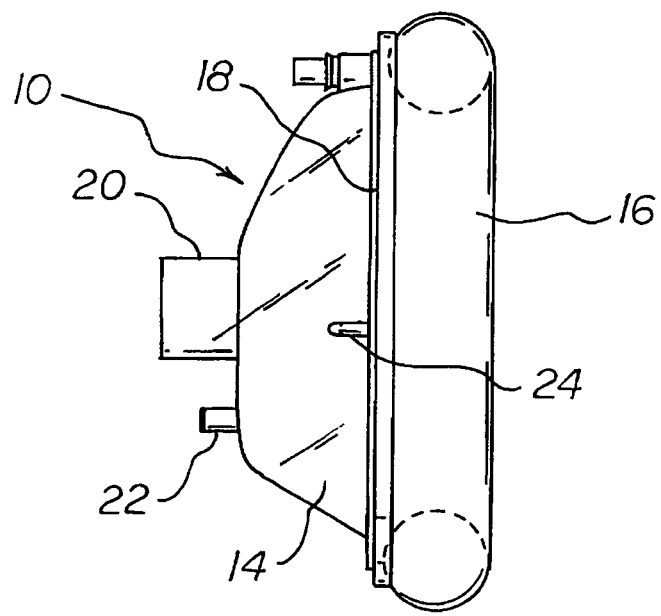
FIG. 4 is a view in elevation of the side of the face mask of FIG. 3 as indicated by lines 4-4.

With reference now to the drawings, and initially to FIGS. 1-9 thereof, there is shown a preferred embodiment of the new and improved respiratory face mask and headstrap assembly of the present invention generally comprising a face mask 10 and a headstrap 12 removably attachable to the face mask for helping to stabilize the mask on the face and head of person, preferably before, during and/or after surgery. The face mask is similar to that fully disclosed in my prior application (Ser. No. 11/809,435), which application has been incorporated herein by reference. The departures of the invention(s) of this application over that disclosed in my prior application will be readily apparent from the ensuing description.

Thus, face mask 10 comprises a shell or receptacle member 14 and a flexible pneumatic (inflatable) cushion sealing member 16. The flexible inflatable cushion/sealing member 16 defines a generally donut-shaped hollow annular member on and along substantially the entire peripheral extent of the shell member and more specifically, preferably is suitably joined to the bottom surface of an annular flange 18 on the peripheral edge or rim of the shell member (see FIGS. 2-5). The shell member preferably is of one-piece or unitary construction fabricated in a known manner (e.g. injection molding) from a synthetic polymeric resin such as polyvinyl chloride, for example, and is transparent so that when face mask 10 is worn on the face of a patient substantially as depicted in FIG. 1, the portion of the patient's face covered by the mask is clearly visible at all times.

As disclosed in my prior application, shell member 14 has a first cylindrical hollow inlet member or port 20 suitably sized to removably receive in snug sliding (and sealing) engagement therein the nipple of a conventional two-branch breathing circuit (not shown) and to define a passageway such that anesthesia gas or other gases are adapted to pass from a source (not shown) through the breathing circuit and the passageway into the interior of shell member 14. The breathing circuit also is adapted to receive returned or exhaust gas or gases through the same passageway and convey such exhausted gas or gases to a conventional gas evacuation or scavenging apparatus (not shown). Shell member 14 also includes a second cylindrical hollow outlet member or port 22. The outside diameter of outlet member 22 suitably is sized to be snugly (and sealingly) removably fitted to one end of a flexible tube (not shown) the other or distal end of which is adapted suitably to be connected to a conventional CO2 monitoring device or capnograph for sensing end-tidal CO2 of a breathing patient.

As further disclosed in my prior application, the unique configuration of the face mask 10 enables the mask readily to be attached to the head of the patient using a relatively simple elastic headband or strap member selectively attachable to the mask shell 14 preferably by way of a pair of protruding integral T-shaped lugs extending oppositely and radially from the flange of the shell member, respectively. In accordance with the present invention, the T-shaped radially-oriented protrusions shown in my prior application (and to which the ends of a simple elastic headstrap removably may be attached) are dispensed with and replaced by a pair of strap fastener members located directly on the upward-facing or top surface of the flange (i.e. the surface opposite to the surface on which the cushion 16 is affixed). The strap fastener members preferably are in the form of substantially cylindrically-shaped riser posts 24, 26 extending substantially perpendicular to the plane of the shell member flange (see FIGS. 1-7) and integral therewith.

Figure 6:
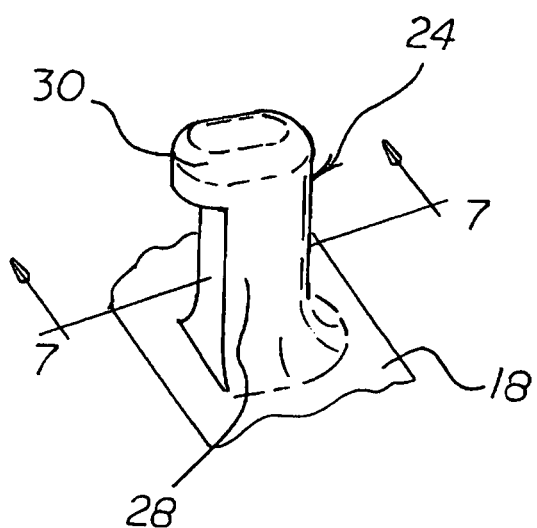
FIG. 6 is a enlarged cross-sectional fragmentary view of the portion of the face mask of FIG. 5 indicated by circle 6.

More specifically, and as shown most clearly in FIGS. 6 and 7, each riser post has a stem portion 28 extending along longitudinal central axis 46 which axis is substantially perpendicular to the upward facing surface of flange 18 and the flat top portion of cushion 16. Preferably, the remote or distal end of each stem portion terminates in an enlarged head portion 30 which is offset with respect to stem portion 28 laterally in a direction toward the sloping wall of shell member 14 (FIG. 5). Thus, substantially as shown in FIG. 5, the enlarged head portion 30 of riser post 24 is offset to the left whereas the enlarged head portion 30 of riser post 26 is offset to the right. In accordance with the invention, the base portion of each stem portion 28 forms an "elbow" with the surrounding surface on flange 18 and the "crook" of that elbow functions to capture and secure the headstrap thereagainst after the enlarged head portion 30 together with stem portion 28 are received through and in a selected opening 44 in headstrap 12 (FIG. 2). Thus, broadly speaking, the riser posts 24, 26 define extremely compact and effective fastening "hooks," respectively, each of which is adapted to anchor or ensnare the corresponding arm extension end portion of the headstrap 12 by being removably slidingly received in a selected opening 44 in each headstrap end portion as will be explained further below. Preferably, riser posts 24, 26 can be formed integrally with flange 18 when shell member 14 is conventionally molded as will be appreciated by those of ordinary skill in the art.

An important feature of the present invention is the location of the riser posts 24, 26 on flange 18 of shell member 14. With special reference to FIG. 3, it will be observed that riser posts 24, 26 are substantially diametrically oppositely located on the flange 18 on an imaginary transverse axis 52 (horizontal as viewed in FIG. 5) which axis is substantially perpendicular to the axis of symmetry 48 of face mask 10. The riser posts 24, 26 also are located on flange 18 relative to an imaginary axis 50 passing transversely though the centerpoint of breathing circuit portal 20 which axis 50 also is substantially perpendicular to axis 48. More specifically, headstrap fastener member location axis 52 is positioned, in accordance with the invention, a distance "d" from the imaginary transverse axis 50. In using face mask 10, it is desired that any displacement of the face mask toward the surface of the face of a patient, caused by tension in the headstrap, will result in substantially even compression of the flexible cushion on opposite sides of the axis 52. Such even cushion compression is important to avoid undesirable "tilting" of the cushion about axis 52, which in turn, might result in imperfect sealing efficacy or an uncomfortable fit. It will be appreciated that the foregoing requirement of obtaining substantially uniform or even sealing cushion compression is met in accordance with the present invention, by positioning location axis 52 proximal to or at the center of mass of mask 10 between the center of breathing circuit portal 20 and the center of CO2 monitoring portal 22. In the preferred embodiment of the present invention, that position is substantially indicated by the distance "d" in FIG. 3.

Without limiting the present invention, and merely for purposes of illustration, a face mask 10 according to the present invention suitable for use on an "average adult" may having the following approximate dimensions:

Height of shell member (measured above flat table to top of port 126)=2.239 inches.

Maximum transverse width in chin region not including flange=3.75 inches.

Intermediate transverse width in mouth region not including flange=3.5 inches.

Minimum transverse width in nose region not including flange=1 inch.

Length measured along axis 48 including flange=5.00 inches.

Distance of center of port 20 from top (nose portion) of mask shell measured along axis 48=2.5 inches.

Spacing "d" between center of port 20 (axis 50) and axis 52 measured along axis 48=0.25 inches.

Width of flange=0.375 inches.

Height of riser posts 24, 26=0.400 inches.

Width or diameter of riser post stem portion=0.110 inches.

Maximum dimension of top surface of enlarged head portion 30 of riser posts 24, 26=0.164 inches.

Figure 8:
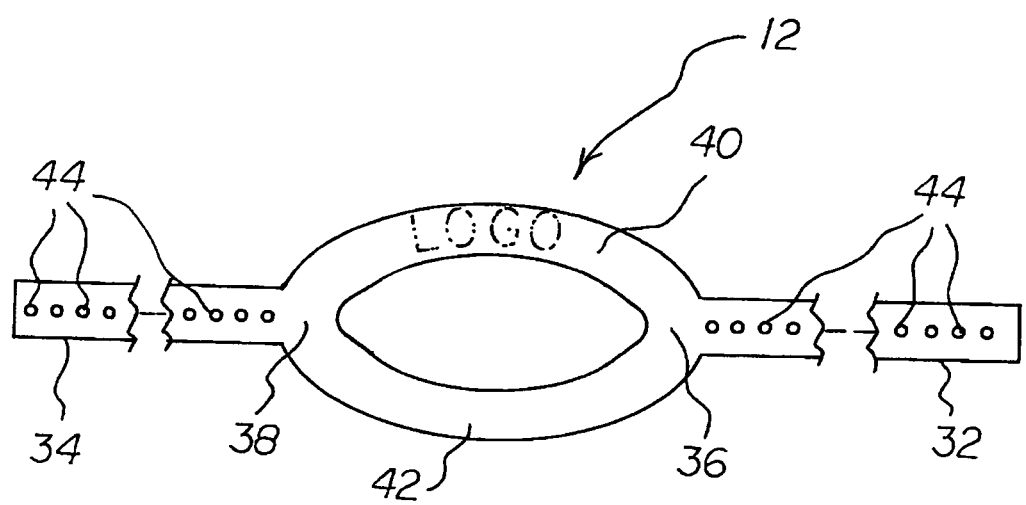
FIG. 8 is a plan view of the headstrap assembly of the present invention.
Figure 9:
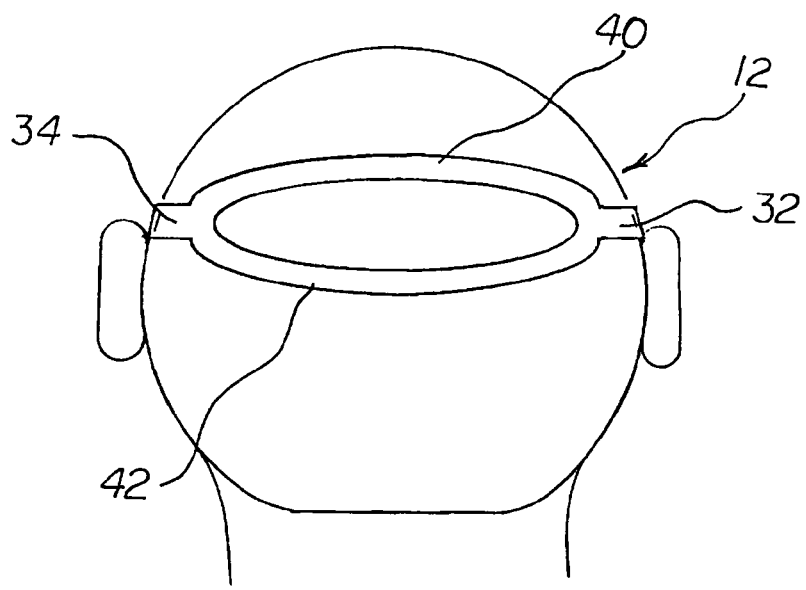
FIG. 9 is a schematic representation showing how the central portion of the headstrap fits the back of an individual's head when it is attached to the face mask in accordance with the present invention.

Although the simple elastic strap disclosed in my prior application may be used to fit the mask 10 on the face of a patient and maintain the mask comfortably stable in its operative position, it has been found to be advantageous to use the improved strap of the present invention shown in FIG. 1, 2 and 8-10. Thus, in accordance with the invention, a new and improved headstrap 12 is provided comprising an annular shaped pressure-distributing central portion and a pair of arm portions extending laterally and oppositely from the central portion. The pressure-distributing central portion is generally oval-shaped and as viewed in FIG. 8 comprises opposed first and second end portions 36, 38 and opposed first and second top and bottom portions 40, 42 joined to end portions 36, 38 substantially as depicted. The center (unlabeled) of the oval-shaped headstrap central portion preferably is open permitting first and second portions 40, 42 to be moved closer or further up or down relative to each other. Laterally extending from end portions 36, 38, respectively, are a pair of first and second arm extensions 32, 34 each terminating distally, remotely and oppositely from the headstrap oval-shaped central portion. A series of evenly spaced openings 44 are centrally disposed substantially as shown (FIG. 8) along substantially the entire longitudinal extent of first and second arm extensions 32, 34, respectively. Openings 44 are sized sufficiently to easily and slidingly receive therethrough the enlarged head portion 30 of each riser post 24, 26. Inasmuch as headstrap 12 preferably is fabricated from a suitable "elastic" or stretchable material (i.e. material with elastic memory), openings 44 may be sized slightly smaller than the maximum transverse dimension of enlarged head portion 30 on riser posts 24, 26. The strap material then will stretch and cause the somewhat smaller openings to open sufficiently in order to easily enable each headstrap arm extension end portion to slide over a corresponding enlarged head portions 30 and then slide down the stem portion 28 to the base thereof when fitted in the manner described below in more detail In use, headstrap 12 is placed under the head of a patient with the central oval-shaped portion engaging the back of the head or skull and with the first and second arm extensions 32, 34 extending laterally (FIG. 8). The face mask 10 then is fitted to the patients's face in the correct position as disclosed in my prior application. Next, the first arm extension 32 is connected to riser post 26 by positioning the distal end of the strap over the riser post and pressing the strap arm extension end portion down until the riser post enlarged end 30 passes through the opening 44 and the arm extension end portion slides down stem portion 28, until ultimately bottoming on the flange 18 substantially as shown in FIG. 2. The other or second arm extension 34 is pulled sufficiently taught and attached to second riser post 24 on the opposite side of mask 10 in the same manner. When so properly attached, the elastic portions 40, 42 will be stretched somewhat across the rear of the patient's head or skull and will be displaced above and below each other substantially as shown schematically in FIG. 9. Such displacement may be adjusted easily merely by repositioning portions 40, 42 after the headstrap has been attached to mask 10 by engaging the headstrap arm extension ends onto riser posts 24, 26 as described above. It will be appreciated that because the first and second portions 40, 42 engage respectively different portions or areas on the rear of the patient's head or skull, these portions 40, 42, particularly when in a stretched or taught condition, will distribute the tensioning pressure of the headstrap over a relatively wide area on the back of the patient's head and thereby will tend to comfortably hold mask 10 in place without either the mask or the headstrap slipping or otherwise being displaced even during relatively long durations of face mask use.

When the mask and headstrap assembly is fitted in operative position as aforesaid, it will be appreciated that the tension pulling force in the stretched portions of the headstrap indicated by arrow 47 in FIG. 2 will cause the strap arm extension end portions to firmly and securely apply an axial fastening force opposite to the axial extent of each riser post 24, 26 along axis 46. This oppositely directed tension, pulling or fastening force automatically will maintain the headstrap arm extension end portions securely bottomed at the juncture where the base or bottom portion of each riser post stem portion meets the flange 18 (i.e. in the "crook" of the "elbow") and thus, in accordance with the invention, provides an extremely effective, efficient and easy-to-use headstrap fastening mechanism suitable for maintaining the mask 10 in a stable and comfortable position on the patient's face for relatively long periods and without requiring excessive strap tension pressure or bulky, cumbersome strap arrangements. It will be particularly noted that because the headstrap extension arm end portions are removably attached to the fastener members on the flange of the face mask shell member in accordance with the invention, the headstrap arm extensions or end portions do not obscure the face mask shell member and the patient's face remains clearly visible during use.

Figure 10:
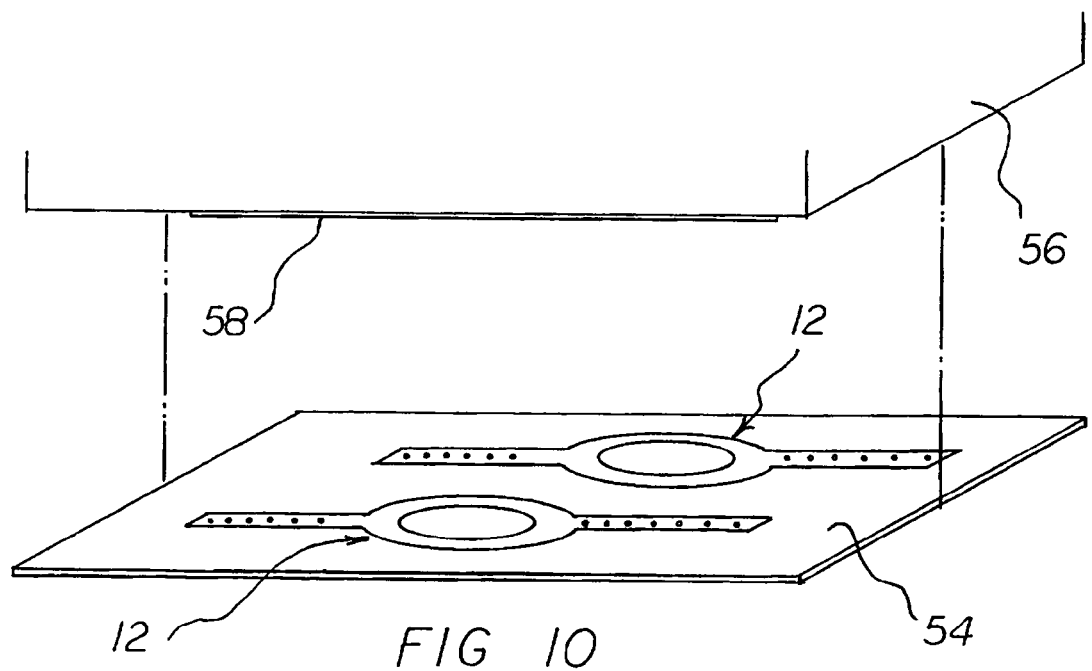
FIG. 10 is a schematic depiction of a tool die-cutting headstraps according to the invention from a web of headstrap material.

Headstrap 12 advantageously may be manufactured efficiently by die-cutting the strap configurations from a web of material 54. This process is schematically depicted in FIG. 10 which shows a punching or cutting die 56 having a die tool 58 formed in the shape of a pair of staggered headstraps. FIG. 10 shows the die tool and web 54 after a pair of headstraps has been cut. By the foregoing staggering arrangement, a maximum number of headstraps may be cut from web of material 54 while minimizing material waste. Any suitable medically acceptable (non-latex) elastic or stretchable material may be employed to fabricate the headstraps 12. A particularly preferred material for use with the present invention is a pliable, durable, synthetic rubber material commercially available from Hygenic Corporation, Akron Ohio, which material prior to this disclosure was widely used to make tourniquets. And although headstrap 12 has been shown as being fabricated of a unitary piece of material, it will be appreciated that the headstrap may be made by taking separate pieces of material or dissimilar material and joining them together as by sewing, gluing, or heat-fusing for example. Without limiting the present invention, and merely for purposes of illustration, headstrap 12 according to the present invention suitable for use with the "average adult" face mask described above, may having the following approximate dimensions:

Length of arm portions 32, 34=6 inches.

Width of arm portions 32, 34=0.75 inches.

Length of central pressure distribution portion measured between end portions 36, 38=8 inches.

Width of central pressure distribution portion=3.00 inches.

Thickness of headstrap=30 mils (0.030 inches).

Diameter of openings 44=0.109 inches.

Spacing between openings 44=0.75 inches.

As to any further manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as defined in the annexed claims.

What is claimed as being new and desired to be protected by Letters Patent of the United States is as follows:

1. An apparatus for delivering gas to a user, comprising:

a disposable face mask;

said disposable face mask including a shell formed of transparent material;

said shell having a top wall adapted to overlie said user's face when the face mask is in use, said top wall being spaced apart from said user's face;

a side wall having a first end formed integrally with said top wall about the periphery of said top wall, said side wall extending toward said user's face in a gradual bend and ending in a second end;

a flange formed integrally with said second end of said side wall in circumscribing relation thereto, said flange extending radially outwardly relative to said shell to define a sealing cushion flange mounting surface proximal to said side wall second end, said sealing cushion flange mounting surface facing oppositely with respect to said top wall and being substantially coplanar throughout substantially its entire circumscribed extent;

a flexible and resilient sealing cushion mounted on said flange mounting surface in circumscribing relation thereto, said sealing cushion adapted to sealingly engage said user's face in the region of the user's nose, mouth, and chin;

said mask being generally pear-shaped and having a narrow first end adapted to fit over a user's nose;

said generally pear-shaped face mask having a middle region adapted to fit over a user's mouth, said middle region having a breadth greater than said narrow first end;

said generally pear-shaped face mask having a broad second end, said broad second end having a breadth greater than the breadth of said middle region, said broad second end of said pear-shaped face mask defining an under-the-chin engagement portion adapted to engage the underside of the user's chin or jaw when said narrow first end is fitted over said user's nose, said middle region fitting over said user's mouth when said sealing cushion is in engagement with said user's face in the region of the user's nose, mouth, and chin;

said sealing cushion having a variable cross-sectional extent when viewed in side elevation with respect to said flange;

said sealing cushion having a portion of first cross-sectional extent in said narrow first end, a portion of second cross-sectional extent in said middle region, and a portion of third cross-sectional extent in said broad second end;

said sealing cushion portion of first cross-sectional extent being smaller than said sealing cushion portion of second cross-sectional extent;

said sealing cushion portion of third cross-sectional extent mounted on said flange forming a portion of said under-the-chin engagement portion defined by said broad second end on said pear-shaped face mask;

a flexible, stretchable headstrap for maintaining said face mask in stable relation to the face and head of said user;

said headstrap having a base and a pair of stretchable, flexible opposed arms extending laterally from said base in opposite directions relative to one another;

each of said arms having a plurality of openings formed therein in linear alignment with one another;

said face mask having a longitudinal axis of symmetry;

said face mask having an inlet port formed therein for admitting gas to the interior of said face mask;

said inlet port enabling passage of exhaled breath from an interior of said face mask;

a first side of said flange providing a first mounting surface;

a pair of riser posts secured to said first mounting surface;

said riser posts of said pair of riser posts being disposed on opposite sides of said longitudinal axis of symmetry of said face mask;

each riser post of said pair of riser posts being integrally formed with said first mounting surface and disposed in upstanding, perpendicular relation to said first mounting surface;

each riser post of said pair of riser posts adapted to be received within a preselected opening of said plurality of openings formed in said arms of said headstrap.

2. The apparatus of claim 1, further comprising:

a first transverse axis, normal to said longitudinal axis of symmetry, extending through a center of said inlet port;

each riser post of said pair of riser posts being disposed on said first mounting surface in registration with said first transverse axis.

3. The apparatus of claim 1, further comprising:

a first transverse axis, normal to said longitudinal axis of symmetry, extending through a center of said inlet port;

a second transverse axis, parallel to said first transverse axis, disposed between said inlet port and said under-the-chin engagement portion;

each riser post of said pair of riser posts being disposed on said first mounting surface in registration with said second transverse axis.

4. The apparatus of claim 1, further comprising:

each riser post of said pair of riser posts including a stem that is perpendicular to said first mounting surface;

a head portion disposed in surmounting relation to each riser post of said pair of riser posts;

each head portion disposed in substantially perpendicular relation to its associated stem, each riser post having an inverted "L" configuration;

said riser posts disposed in mirror-image relation to one another;

each head portion extending toward said longitudinal axis of symmetry of said face mask.

5. The apparatus of claim 4, further comprising:

each of said openings having a size slightly smaller than that of each head portion;

each laterally disposed arm of said headstrap being firmly secured to an associated riser post when each stem is received within a preselected opening.

\* \* \* \* \*